United States Patent

Van Oorschot et al.

[11] Patent Number: 6,008,426
[45] Date of Patent: Dec. 28, 1999

[54] PROCESS FOR CATALYTIC CONVERSION OF OLEFINS

[75] Inventors: Cornelius W. M. Van Oorschot, Brasschaat, Belgium; Michiel Makkee, CE Rockanje, Netherlands; Marcel J. G. Janssen; Wilfried J. Mortier, both of Kessel-Lo, Belgium

[73] Assignee: Exxon Chemical Patents Inc., Houston, Tex.

[21] Appl. No.: 09/089,276

[22] Filed: Jun. 2, 1998

Related U.S. Application Data

[63] Continuation-in-part of application No. 08/483,601, Jun. 7, 1995, abandoned, which is a continuation of application No. 08/333,931, Nov. 3, 1994, abandoned, which is a continuation of application No. 07/955,740, Feb. 7, 1993, abandoned.

[30] Foreign Application Priority Data

Jun. 7, 1990 [GB] United Kingdom ............. 9012725

[51] Int. Cl.$^6$ .................................................. C07C 2/04
[52] U.S. Cl. .......................... 585/510; 585/500; 585/671
[58] Field of Search .................................. 585/500, 510, 585/671

[56] References Cited

U.S. PATENT DOCUMENTS

2,217,252  10/1940  Hoog .
4,503,282   3/1985  Sikkenga .

FOREIGN PATENT DOCUMENTS

0034444   8/1981  European Pat. Off. .
0 071 199  9/1983  European Pat. Off. .
0 152 918  8/1985  European Pat. Off. .

*Primary Examiner*—Elizabeth D. Wood
*Attorney, Agent, or Firm*—Bradley A. Keller

[57] ABSTRACT

The conversion of n-olefins, particularly n-butene, by skeletal isomerization, or by dimerization optionally with cracking, may be selectively carried out using as a catalyst a molecular sieve, such as a zeolite or silica/alumina phosphate, which has been ion exchanged with a cation to provide a Lewis acid site. No steam activation of the molecular sieve is required.

13 Claims, 1 Drawing Sheet

□ 0 BARS ABOVE ATMOSPHERIC PRESSURE
+ 4 BARS ABOVE ATMOSPHERIC PRESSURE
◇ 8 BARS ABOVE ATMOSPHERIC PRESSURE

PROCESS FOR CATALYTIC CONVERSION OF OLEFINS

This patent application is a continuation-in-part of U.S. patent application Ser. No. 08/483,601, filed Jun. 7, 1995, now abandoned; which is a continuation of Ser. No. 08/333,931, filed Nov. 3, 1994, now abandoned; which is a continuation of Ser. No. 07/955,740, filed Feb. 7, 1993, now abandoned.

FIELD OF INVENTION

The present invention relates to a process for conversion of an n-olefin to different unsaturated compounds.

BACKGROUND OF THE INVENTION

Some unsaturated compounds are readily available e.g. from fossil fuel sources. However the demand for certain unsaturated compounds is greater than for others. There is therefore a need to interconvert unsaturated compounds. In particular, n-olefins may be converted e.g. by skeletal isomerization or by dimerization optionally followed by cracking. Isobutene is present in the C4 products obtained from steam-cracking of naphthas or from catalytic cracking of high boiling fuel cuts. Other $C_4$ products such as n-butene (1-butene, cis-butene-2, trans-butene-2, and mixtures thereof) are also present. Demand for isobutene is increasing and there is therefore a need for a process for converting n-butene efficiently to isobutene.

Several processes are known for the skeletal isomerization of n-olefins e.g. the production of isobutene from n-butene. Such conversion has previously been carried out using an amorphous catalyst. For example, EP-A-152918 describes a disproportionation and isomerization catalyst for olefins which comprises silica and molybdenum oxide together with titanium dioxide as promoter.

U.S. Pat. No. 2,217,252 describes the use of natural and synthetic zeolites such as analcime, chabazite, heulandite, natrolite and thomsonite in the interconversion of olefins.

A process potentially of commercial use for the skeletal isomerization of an olefin is the so-called "Snamprogetti process". In this process the olefin is in contact with an activated alumina catalyst at high temperature (about 450° C.).

The WHSV (weight hourly space velocity) is a measure of the throughput of olefin which is used in continuous use of the catalyst. At 450° C. a WHSV of 2 $hr^{-1}$ is common in the Snamprogetti process. Under these conditions n-butene yields approximately 30% isobutene with a selectivity of 75%. The catalyst has a life of at least 8 hours before it is necessary to regenerate it.

If the WHSV is increased to more than 12 $hr^{-1}$ the isobutene yield drops to around 8%.

Another fluorine- or chlorine-containing "activated" alumina catalyst is described in EP-A-0071199. The catalytic activity is comparable with the Snamprogetti catalyst; the isobutene selectivity is higher.

U.S. Pat. No. 4,503,282 describes the use of AMS-IB boro silicate, a boron containing ZSM-5 type zeolite, in the interconversion of olefins. This catalyst operates at low WHSV (commonly 2 $hr^{-1}$ or less) and high temperature (400–600° C.). The reported selectivities are lower in general than those of the amorphous alumina based catalysts.

Catalysts are also used in the dimerization of n-olefins, but these are not without their problems. It is known to use as a catalyst solid phosphorous acid on kieselguhr. The catalyst cannot be regenerated and disposal of large quantities of catalyst as land-fill material is no longer acceptable.

SUMMARY OF THE INVENTION

Figure 1:
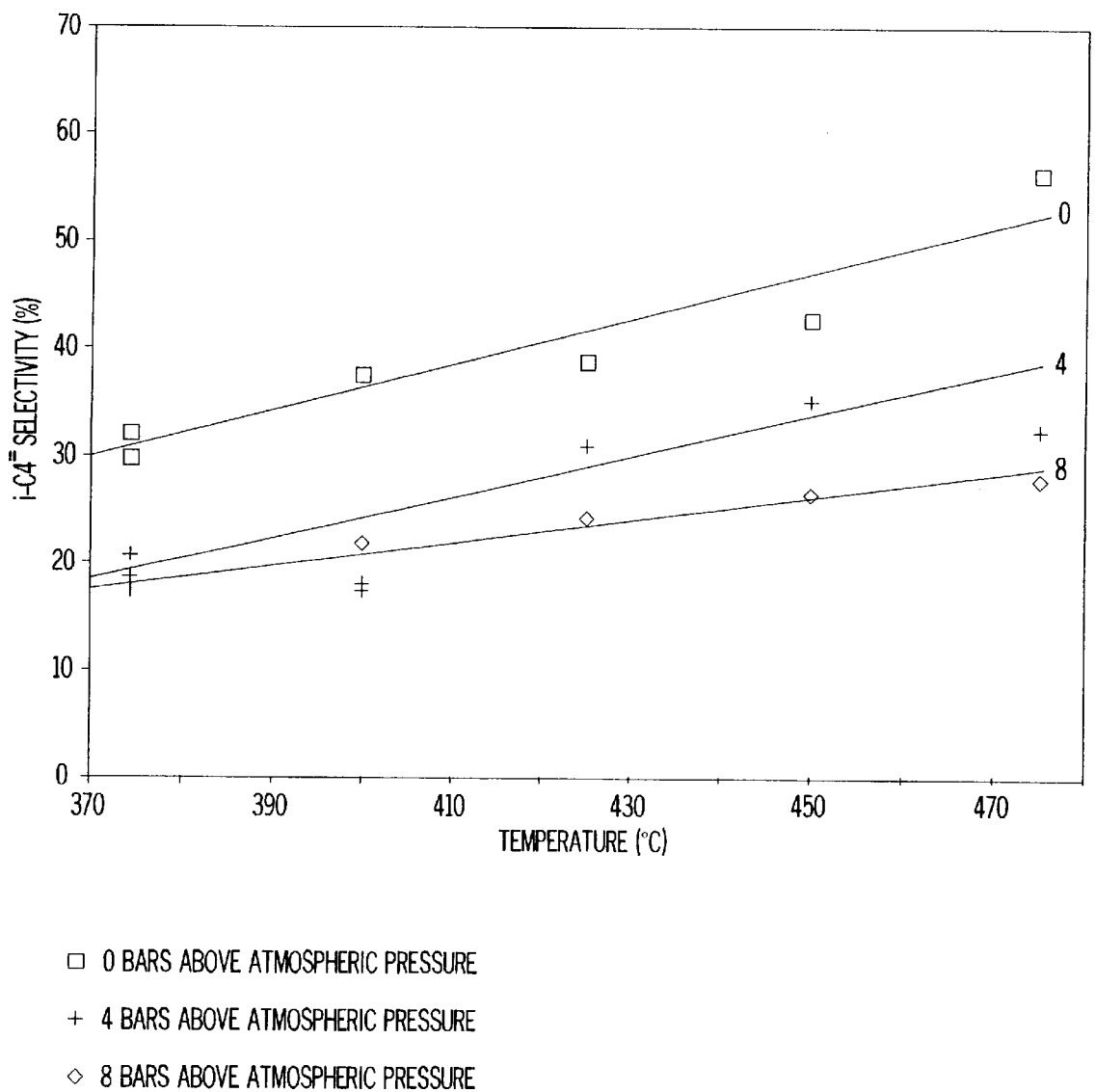
FIG. 1 is a plot showing the selectivities to isobutene as a function of temperature at different pressures.

A process for conversion of an olefin to different unsaturated compounds, said process comprising: providing said n-olefin in a liquid or a vapour phase wherein said n-olefin comprises in the range of from 3 to about 9 carbon atoms; and contacting said n-olefin with a catalyst under conditions effective to convert said n-olefin to different unsaturated compounds, wherein said catalyst comprises a molecular sieve which has been ion-exchanged with a cation to provide Lewis acid sites wherein a majority of said Lewis acid sites comprising cations selected from the group consisting of magnesium, calcium, strontium, barium, copper, nickel, cobalt and mixtures thereof.

DETAILS OF THE INVENTION

The applicants sought a catalytic process for the skeletal isomerization or dimerization and optional cracking of olefins, particularly n-olefins of 4 to 6 carbon atoms, which had a good selectivity and yield of the desired olefin for a given WHSV, which had an acceptable catalytic life and which used a catalyst which could be easily regenerated.

Previous research aimed at producing catalysts for the interconversion of unsaturated compounds has been directed to compositions, generally amorphous, which contain Bronsted acid sites i.e. sites which are capable of donating a proton, $H^+$. It was believed that interaction between the unsaturated compound and a proton on the surface of the catalyst facilitated the desired conversion. The present inventors have surprisingly found that a molecular sieve which has been ion exchanged with a cation to give a Lewis acid site is a particularly good catalyst for the interconversion of unsaturated compounds. In particular, the inventors have discovered that the molecular sieve does not need to be treated or activated with steam at high temperatures to be suitable for use. Similarly, a molecular sieve catalyst after ion-exchange does not need steaming at elevated temperatures to achieve the desired catalytic performance.

The present invention provides a process for conversion of an n-olefin in the range of from 3 to about 9 carbon atoms to another different unsaturated compound comprising contacting the olefin in the liquid or vapour phase with a catalyst which comprises a molecular sieve which has been ion-exchanged with a cation to provide a Lewis acid site. Steam activation of the molecular sieve prior to or after the ion-exchange is not needed to achieve the desired catalytic performance.

The catalytic process of the present invention has the advantage that it may be used to perform either skeletal isomerization or dimerization and that the dimerization may optionally be combined with cracking. The dominant reaction may be selected by choosing the appropriate reaction conditions bearing in mind the particular catalyst being used.

The catalyst is a molecular sieve, such as a zeolite or a silica/alumina phosphate (SAPO) which should contain Lewis acid cation sites.

The zeolite may be selected from, for example, zeolite Y, zeolite beta, ZK-5, ZSM-5, ZSM-12, ZSM-22 or ZSM-23.

Other suitable molecular sieves include, but are not necessarily limited to SAPO's.

The catalyzed reaction is carried out in the presence of Lewis acid and base sites. This combination of sites may be provided suitably by a molecular sieve. The base sites are present inherently in the molecular sieve e.g. the $O^{2-}$ ions in the zeolite framework. The cations are present to provide electroneutrality, e.g. divalent cations such as alkaline earth metal cations, provide Lewis acid sites of the desired strength.

It is particularly useful to use as a catalyst a molecular sieve and to ion exchange it with cations. Other ways of incorporating metal cations, such as an incipient wetness method, dry mixing, or wet mixing, or dry contacting also may be used. The ion exchanged cations present in the sieve do not form an integral part of the framework i.e. they are not covalently bound into the Si/Al/O network of a zeolite. Thus when taking part in the olefin conversion it is not necessary for cations to be removed from the framework and the framework is not weakened. The catalyst composition may be easily controlled by selecting the particular molecular sieve and exchange cations.

In a sieve such as a zeolite the framework is composed of tetrahedra of $SiO_4$ and $AlO_4$. The presence of the aluminum produces a charge imbalance in the framework. In a SAPO, some of the $(Al, P)O_4$ tetrahedra are replaced by $(Si, Al)O_4$ tetrahedra, which also produce a charge imbalance. To achieve electroneutrality cations are introduced into the sieve. In synthetic zeolites these cations are often alkali metals such as sodium or potassium, or protons.

Such alkali metal cations may be ion exchanged with other cations which provide stronger Lewis acid sites. Although trivalent cations may be used in the ion exchange the Lewis acid sites produced are generally too strong and it is preferred to use divalent cations. Suitable cations are those whose inclusion in zeolites is known to those of skill in the art, for example, magnesium, calcium, strontium and barium ions. Other divalent cations may also be used to provide Lewis acid strength, for example copper, nickel, and cobalt.

The molecular sieves containing cations will be referred to hereafter by the cation hyphenated to the type of molecular sieve e.g. Mg-beta will be used to denote a zeolite beta containing magnesium ions.

The electronegativity of a zeolite (a function of the composition and the structure type) determines the Lewis acid and base site strength. The electronegativity of a molecular sieve may be varied by methods known to the skilled person, such as ion exchange and/or by changing the $Si/Al_2$ ratio.

In a typical ion exchange, the solid material is mixed with an aqueous solution containing sufficient amount or excess of cation to be introduced. On an experimental scale 10 g of solid, for example, may be mixed with 15–25 mls of solution. The mixture is stirred eventually at elevated temperature and the solid is then washed prior to use.

The particular catalyst which will be suitable for any process will depend on the features required for the process. Certain processes will need shorter contact times than others.

When selecting a catalyst for the present process, certain physical attributes of the catalyst should be considered. In general, the higher the ratio of $Si/Al_2$ the greater the average electronegativity of the catalyst.

A $Si/Al_2$ ratio of 120 such as may be present in a molecular sieve will result in a higher electronegativity than a $Si/Al_2$ ratio of 70. A "high" electronegativity tends to lead to a catalyst which is more active or stable than a catalyst of lower electronegativity. A high $Si/Al_2$ ratio is therefore preferred in the molecular sieve.

The catalyst becomes deactivated during use by the deposition of coke. If the catalytically active sites are far apart then the deactivation may be reasonably slow. Active sites which are far apart i.e. a low active site density are therefore preferred.

One of the factors relating to the density of Lewis acid sites is the cation exchange capacity of the sieve. A sieve which requires the presence of cations for its electroneutrality will have a cation exchange capacity (CEC) generally expressed in meq/g (dried sieve). The higher the CEC, the more closely positioned the active sites for this process. Sieves with a low CEC are therefore preferred in general. The following table gives an indication of CEC values for some of the sieves which may, be used in the present process.

| SIEVE | CEC (meq/g(dried sieve)) | $SiO_2/Al_2O_3$ |
| --- | --- | --- |
| Y | 4.53 | 1.16 |
| Mordenite | 2.62 | 2.5 |
| ZSM-12 | 1.72 | 4.17 |
| ZSM-22 | 1.35 | 5.5 |
| ZSM-23 | 1.35 | 5.5 |
| SAPO-11 | 0.04 | — |

When the silica-alumina ratio increases this results in a decrease in the cation exchange capacity.

Improved stability of catalyst is also seen when the channel dimensions i.e. pore size/void space of the catalyst are reduced. By decreasing the internal volume, coke precursors are prevented from reaching the critical size which would render them unable to leave the pore system. Coke formation is reduced and the deactivation rate of the catalyst will thereby be reduced. If the pore size is too small the catalytic activity is adversely affected. A medium pore size which appears to be the optimum is a T atom ring size of 8 to 12.

A particularly preferred catalyst which has active sites which are far apart, and limited channel dimensions is SAPO-11 i.e. a silica/alumina phosphate which can be synthesized by known methods. Magnesium ions, calcium ions, and mixtures thereof are preferred divalent cations for providing Lewis acids in SAPO-11.

The catalyst may be used in the form of a powder or an extrudate, although the extrudate is usually preferred in industrial processes.

The molecular sieves do not need or require steam activation to be useful for preparing the catalysts. In other words, the molecular sieves can be used in the absence of steam treatment or steam activation. Similarly, the catalysts may provide the desired performance in the absence of steam treatment or steam activation.

The process of the present invention may be used to isomerize or dimerize and optionally crack n-olefins of 3 to about 9 carbon atoms particularly n-olefins of 4 to 6 carbon atoms i.e. n-butene, n-pentene and n-hexene, especially n-butene. N-butene, n-pentene and n-hexene include all the respective linear isomers and mixtures thereof.

The olefin conversion process may be carried out by charging a reactor such as a stainless steel (SS) reactor with the catalyst and then activating the catalyst. This is generally achieved by continuously passing an inert gas such as nitrogen through the catalyst for from about one to about three hours at elevated temperature. No steam activation is needed. The temperature and pressure in the reactor are then adjusted to the conditions under which it is desired to carry out the reaction. The olefin is then fed through the catalyst, optionally with an inert diluent.

When the reaction temperature is in the range of from about 250° C. to about 500° C. especially from about 375° C. to about 475° C. and the reaction pressure is in the range of from about 0.08 MPa to about 0.12 MPa, especially at about atmospheric pressure, the major reaction will be the skeletal isomerization of the n-olefin. Thus n-butene will be isomerized to give isobutene. At higher temperatures the secondary $C_4$ reactions such as alkylation, dimerization, hydrogenation cracking are suppressed but the formation of the isobutene is also less. The above ranges are believed to provide the optimum amount of product with acceptably small levels of side products.

Reducing the temperature and increasing the pressure will tend to favor formation of the dimerized products. When the reaction temperature is in the range of from about 80° C. to about 250° C., especially around 200° C., and the reaction pressure is relatively high e.g. greater than 10 barg, the major reaction will be the dimerization of the n-olefin. Thus n-butene will be dimerized to give unsaturated $C_8$ compounds.

On the other hand if the reaction temperature is maintained at a temperature comparable with that used for isomerization i.e. In the range of from about 250° C. to about 500° C. but the pressure is increased from isomerization pressure to the range from about 0.12 MPa to about 2 Mpa, this favors the formation of disproportionated dimerization products; for example n-butene under these reaction conditions will form propene and pentenes.

Using the present process the skilled person can control the form of catalyst used by selecting a particular molecular sieve structure and pore size and ion exchanging the sieve with the desired cation to provide Lewis acid sites in the sieve. Once the catalyst has been selected, the reaction conditions appropriate for the desired product using that catalyst can be established by adjusting the temperature and pressure based on the knowledge of which products are favored by increasing or decreasing the temperature or pressure.

The catalyst will eventually require regeneration to rid it of the coke deposits which gradually build up the pores. The regeneration may be easily carried out by a coke burn in air at a temperature in the range of from about 350° C. to about 700° C., preferably in the range of from about 450° C. to about 550° C.

The following examples illustrated the invention.

EXAMPLE 1

Skeletal Isomerization

A SS reactor was charged with 1.0 g of catalyst, particles size 210 μm<d<600 μm.

Prior to use the catalyst was activated at 500° C. for 2 hours under a continuous flow of nitrogen (50 ml/min). After activation the reactor temperature was changed to the desired temperature.

In all experiments 1-butene was used as a feed. If, necessary the feed stream was diluted with nitrogen.

The reactions were run for different times, depending on the deactivation rate of the catalyst.

Samples of the product stream were analyzed every hour by gas chromatography (GC) on line, using an $Al_2O_3$/KCl plot column.

The following test conditions were used:
Temperature: 375° C.
Pressure: atmospheric
WHSV: 1
HC/Diluent: 1:3
Diluent: nitrogen
The results are shown in Tables I and II.

The time on stream taken to reach a conversion level of 10% can be used to measure the stability of the catalyst; the longer this time, the more stable the catalyst.

With decreasing Lewis acid strength (in the order of Mg(II), Ca(II), Sr(II) and Ba(II)), the following observations were made:
increase in isobutene selectivity;
increase in catalyst life;
increase in the heavies selectivity;
decrease in lights selectivity and
decrease in hydrogen transfer (ratio of C4 and C3=).

TABLE I

RESULTS FOR ZEOLITE Y

| | CATALYST | | | |
|---|---|---|---|---|
| | MgY | CaY | SrY | BaY |
| Time (10% conversion)* | 2.0 | 1.5 | 5.3 | 7.3 |
| yield isobutene % | 2.3 | 1.6 | 2.1 | 2.8 |
| sel. lights (1) % | 71 | 60 | 51 | 29 |
| sel. heavies (2) % | 6 | 24 | 28 | 43 |
| Approach to Isob. eq. (%) | 5 | 4 | 5 | 7 | sel. = Selectivity for
*Time in Hours
(1) Lights are defined as $C_1$, $C_2$, $C_2^=$, $C_3^=$ and $C_4$.
(2) Heavies are defined as $C_5^{+}$'s

TABLE II

| | CATALYST | | | |
|---|---|---|---|---|
| | Zeolite Y | Zeolite β | | Zeolite SAPO-11 |
| Sample | CaY | Caβ | Caβ | Ca-SAPO-11 |
| (SiO2/Al2O3) | 5 | 28 | 51 | n.a. |
| conversion (at 3 hours) | 7 | 26 | 83 | 75 |
| yield isobutene (%) | 1 | 12 | 13 | 24 |
| sel. lights (1) (%) | 60 | 37 | 34 | 25 |
| sel. heavies (2) (%) | 24 | 15 | 50 | 43 |
| Approach to isob. eq. (%) | 4 | 29 | 31 | 57 |

(1) Lights are defined as $C_1$, $C_2$, $C_2^=$, $C_3^=$ and $C_4$.
(2) Heavies are defined as $C_5^{+}$'s The deactivation rate of zeolite Y is high. It is known from the open literature that coke formation increases with the radius of the zeolite channels and cages. Zeolite Y is one of the larger pore zeolites, therefore showing a fast deactivation. Zeolite Beta in comparison with zeolite Y, has fewer acid sites and also has smaller channels.

A comparison of the results for Ca-Beta and Ca-Y shows that smaller zeolite channels and lower acid site density resulted in a lower deactivation rate and a higher isobutene selectivity. For Ca-Beta with $SiO_2/Al_2O_3$ ratio of 51 the acid site density is lower than that of Ca-Beta with an $SiO_2/Al_2O_3$ ratio of 28. Therefore, the deactivation rate of Ca-Beta(51) is lower and the isobutene yield is higher than that of Ca-Beta(28). For the SAPO-11 molecular sieves, the acid site density is very low and the channel radius is smaller than for zeolite Y and zeolite Beta. The results for Ca(II) exchanged SAPO-11 as indicated in Table II showed an isobutene yield of 24 wt % and a very low deactivation rate.

Thus the smaller pores in zeolite beta in comparison with zeolite Y led to a lower deactivation rate of the catalyst, i.e. a suppression of side reactions.

The even lower deactivation rate of the SAPO-11 catalyst was also due to the small pore size and also the isolated acidic sites.

Varying the WHSV does not affect the initial activity or selectivity of the catalyst. However, deactivation is affected by WHSV; the lower the WHSV, the longer the catalyst life.

Regeneration

The catalysts were each regenerated by treating with 5% oxygen in nitrogen at 550° C. When re-used in the isomerization process they showed the same initial activity/deactivation rate but a slight change in selectivities. The Ca-SAPO-11 selectivity for isobutene was slightly down (31 to 28), for lights was slightly lower (24 to 18) and for heavies slightly up (45 to 54).

FIG. 1 shows the variation in the selectivity for isobutene with varying temperature and pressure using a Ca-SAPO-11 catalyst. It can be seen from this that high temperatures and low pressures favor production of the skeletally isomerized product.

EXAMPLE 2

Skeletal Isomerization Using SAPO-11 Extrudates

Commercially available SAPO-11 extrudates (as received, Mg(II)- and Ca(II) exchanged forms) were tested for the skeletal isomerization of n-butenes. In all experiments the selectivity for isobutene is somewhat higher than in the powder experiments. The deactivation rate for the extrudates is slightly higher. The time required to reach the maximum yield of isobutene is 24 hours for the Mg(II)- and Ca(II) exchanged extrudates, 48 hours for the as received extrudates and 1–2 hours for the powders. The catalyst life of the SAPO-11 extrudates is over 140 hours run length and the isobutene selectivity is around 125% of the thermodynamic equilibrium. The high yield of isobutene over molecular sieve catalysts (125% of thermodynamic equilibrium) can be explained as follows: 1) one part of isobutene is formed via the skeletal isomerization and 2) the other part of isobutene is formed via a dimerization of butenes to octenes and followed by selective cracking of these octenes to propene, pentenes and especially isobutene (and other butenes). The results are shown in Table III.

TABLE III

| MATERIAL | Ca-SAPO-11 powder | SAPO-11 extrudates | Alumina modified (Snamprogetti) |
|---|---|---|---|
| Conversion (%) | 63 | 48 | 35 |
| yield isobutene (%) | 29 | 40 | 24 |
| yield lights (1) (%) | 22 | 5 | 4 |
| yield propene (%) | 19 | 5 | 1–2 |
| yield heavies (2) (%) | 12 | 4 | 7 |
| approach to i-$C_4^=$ equil. (%) | 116 | 128 | 71 |
| life time (hrs) | >25 | >140 | 8 |

(1) Lights are defined as $C_1$, $C_2$, $C_2^=$, $C_3$, $C_3^=$ and $C_4$.
(2) Heavies are defined as $C_5^{+}$'s

EXAMPLE 3

Production of Propene Using SAPO-11 Extrudates

A SS reactor was charged with 1.0 gram of commercially available SAPO-11 extrudates (as received, Ca(II) exchanged form), particle size 210 μm<d<600 μm. Prior to use the catalyst was activated at 500° C. for 2 hours under a continuous flow of dried nitrogen (50 ml/min). After activation the reactor temperature was lowered to the desired temperature.

In the experiments 1-butene was used as a feed, diluted with nitrogen. The pressure drop over the reactor was <0.1 barg. Product analysis was done by gas chromatography on line, using an $Al_2O_3$/KCl plot column.

The following test conditions were used:

Temperature: 475° C.

Catalyst: Ca-SAPO-11 extrudates

WHSV: 1

HC/Diluent: 1:3

Diluent: nitrogen

The results are shown in Table IV.

TABLE IV

| Material | Ca-SAPO-11 | extrudates |
|---|---|---|
| Conversion (%) | 48 | 58 |
| yield isobutene (%) | 40 | 27 |
| yield lights (1) (%) | 5 | 18 |
| yield propene (%) | 5 | 17 |
| yield C5's (2) (%) | 4 | 12 |
| yield heavies (2) (%) | 1 | 1 |
| pressure (barg) | 0 | 2 |

(1) Lights are defined as $C_1$, $C_2$, $C_2^=$, $C_3$, $C_3^=$ and $C_4$'s.
(2) $C_5$'s are defined as $C_5^=$'s and $C_5$'s.
(3) Heavies are defined as $C_5^{+}$'s.

(1) Lights are defined as $C_1$, $C_2$, $C_2^=$, $C_3$, $C_3^=$ and $C_4$'s.

(2) $C_5$'s are defined as $C_5^=$'s and $C_5$'s.

(3) Heavies are defined as $C_5^{+}$'s.

An increase in pressure results in selective cracking of the dimerisation-formed octenes into the valuable propene and pentenes.

EXAMPLE 4

Dimerization

The dimerization of 1-butene was studied in a stainless steel fixed bed reactor. The temperature was 200° C., pressure was 10 barg and WHSV of 1.5. Prior to use the catalysts were dehydrated and activated at 500° C. for 16 hours under dried air at a flow rate of 1000 (ml/ml(cat)×hrs). The pressure drop over the reactor was in all experiments <0.1 barg. Product analysis was done by gas chromatography using a squalane column with hydrogen as carrier gas. The average carbon number distribution number was determined off-line with gas chromatography using a 13× molecular sieve column. For both GC analyses, the sample was hydrogenated in situ in the injector system of the GC over a platinum on alumina catalyst in order to simplify the analysis, by hydrogenation of the olefins into paraffins. Various types of catalyst/zeolites were tested: molecular sieves SAPO-11 extrudates (obtained from Union Carbide, crystal size distribution 0.5 μm–5 μm (main distribution 1.3 μm–2.2 μm)) and zeolite Beta (silica-alumina ratio of 51). The catalyst extrudates were crushed to a particle size distribution from 0.2 mm–0.6 mm in order to eliminate diffusion phenomena and reactor wall effects.

The results are shown in Tables V to VIII.

TABLE V

Dimerization of 1-butene over SAPO-11 extrudates.

| Catalyst | SAPO-11 | extrudates |
|---|---|---|
| Time (hours) | 10 | 20 |
| Conversion (%) | 13 | 10 |
| Branchiness | 1.8 | 1.8 |
| Av. Carbon Number | | |
| C5 | 0 | 0 |
| C6 | 10 | 5 |
| C7 | 13 | 5 |
| C8 | 43 | 48 |
| C9 | 9 | 6 |
| C10 | 3 | 2 |
| C11 | 3 | 3 |
| C12 | 13 | 6 |
| C12+ | 0 | 5 |

Temperature: 200° C., Pressure: 10 barg and WHSV: 1.5
Branchiness is defined as:

$$\frac{3^* \text{ tribranched } C_8\text{'s} + 2^* \text{ dibranched } C_8\text{'s} + 1^* \text{ monobranched } C_8\text{'s} + 0^* \text{ linear } C_8\text{'s}}{\Sigma C_8\text{'s}}$$

The random carbon number distribution and the residues on the catalyst indicate that the overall acidity of the SAPO-11 is high (high oligomerization and cracking rates). Cation exchange of zeolites/molecular sieves can tailor the strength of the acidity to produce catalysts for the present process.

TABLE VI

Dimerization of 1-butene over Mg-SAPO-11 extrudates.

| Catalyst | Mg-SAPO-11 | extrudates |
|---|---|---|
| Time (hours) | 10 | 20 |
| conversion (%) | 13 | 12 |
| Branchiness | 1.8–1.9 | 1.7–1.8 |
| Av. Carbon Number | | |
| C5 | 0 | <0.2 |
| C6 | 6 | <0.3 |
| C7 | 2 | 0.5 |
| C8 | 92 | 99 |
| C9 | 0 | 0 |
| C10 | 0 | 0 |
| C11 | 0 | 0 |
| C12 | 0 | 0 |
| C12+ | 0 | 0 |

Temperature: 200° C., Pressure: 10 barg and WHSV: 1.5.

As can be seen in Table VI, the activity of a magnesium exchanged SAPO-11 extrudates catalyst is the same as for the untreated SAPO-11 extrudates. The branchiness is 1.6. The selectivity to the C8's is exceptionally high (>98%).

For the dimerization reaction of butenes over a non-ion exchanged zeolite catalyst the presence of the transition metal nickel its oxidation state on the catalyst support is essential. SAPO-11 extrudates as received were exchanged with nickel and subsequently in situ in the reactor activated at 500° C. for 16 hours under dried air flow. The nickel exchange level was not analyzed.

TABLE VII

Dimerization of 1-butene over Ni-SAPO-11 extrudates.

| Catalyst | Ni-SAPO-11 | extrudates |
|---|---|---|
| Time (hours) | 10 | 50 |
| Conversion (%) | 2 | 2 |
| Branchiness | 1.8 | 1.7 |
| Av. Carbon Number | | |
| C5 | 0 | 0 |
| C6 | 0 | 1 |
| C7 | 2 | 3 |
| C8 | 92 | 94 |
| C9 | 2 | 0 |
| C10 | 0 | 0 |
| C11 | 0 | 0 |
| C12 | 4 | 2 |
| C12+ | 0 | 0 |

Temperature: 200° C., Pressure: 10 barg and WHSV: 1.5.

As can be seen in Table VII the activity of the nickel exchanged SAPO-11 extrudates is, in comparison with the previously tested catalysts (SAPO-11 and Mg-SAPO-11), very low.

The activity maintenance of this catalyst is good. Even up to 100 hours on stream the conversion level remains unchanged (2%). The selectivity to C8's and the branchiness of this fraction are comparable to those of Mg-SAPO-11 (>92% and 1.7–1.8, respectively).

In zeolite Beta the number of cation exchangeable sites is higher than in SAPO-11 and it might be expected that nickel exchanged zeolite Beta would be more active. Nickel exchanged zeolite Beta was activated in situ in the reactor at 500° C. for 16 hours under dried air. The nickel exchange level was not analyzed.

TABLE VIII

Dimerization of 1-butene over Ni-zeolite Beta.

| Catalyst | Ni-Beta ($SiO_2/Al_2O_3 = 51$) | | | |
|---|---|---|---|---|
| Time (hours) | 10 | 20 | 50 | 130 |
| Conversion (%) | 14 | 11 | 13 | 7 |
| Branchiness | 1.8 | 1.7 | 1.7 | 1.6 |
| Av. Carbon Number | | | | |
| C5 | | | 0 | 0 |
| C6 | | | 5 | 2 |
| C7 | | | 4 | 3 |
| C8 | | | 45 | 56 |
| C9 | | | 5 | 5 |
| C10 | | | 1 | 2 |
| C11 | | | 4 | 3 |
| C12 | | | 30 | 27 |
| C12+ | | | 6 | 2 |

Temperature: 200° C., Pressure: 10 barg and WHSV: 1.5.

As can be seen in Table VIII the activity of nickel exchanged zeolite Beta is much higher (14% conversion versus 2% for Ni-SAPO-11). Although the initial conversion level drops over the first 20 hours, the conversion level remains unchanged up to 130 hours on stream (still 7% conversion up to 130 hours on stream). The branchiness of the C8 fraction is good (1.6–1.8). After the run on the catalyst some amounts of C18 and C22 were observed. The random carbon number distribution and the amounts of residues on the catalyst indicate that the overall acidity of the Beta is rather high (high oligomerization and cracking rates).

Persons of ordinary skill in the art will recognize that many modifications may be made to the present invention without departing from the spirit and scope of the present invention. The embodiment described herein is meant to be illustrative only and should not be taken as limiting the invention, which is defined by the following claims.

We claim:

1. A process comprising
incorporating cations at a surface of a molecular sieve catalyst to produce Lewis acid sites at said surface, wherein said cations are selected from the group consisting of magnesium, calcium, strontium, barium, copper, nickel, cobalt, and mixtures thereof,
contacting said catalyst with an n-olefin under given conditions, wherein said n-olefin comprises from about 3 to about 9 carbon atoms,
wherein said conditions are effective to achieve a result selected from the group consisting of skeletal isomerization and dimerization of said n-olefin to produce a reaction product, wherein said molecular sieve catalyst is used in the absence of activation with steam prior to contacting said catalyst with said n-olefin.

2. A process according to claim 1 wherein said molecular sieve comprises a zeolite or a silica/alumina phosphate (SAPO).

3. A process according to claim 2 wherein said molecular sieve is zeolite Y, zeolite Beta, ZK-5, ZSM-5, ZSM-12, ZSM-22, ZSM-23 or a SAPO-11.

4. A process according to claim 3 wherein said cation is selected from the group consisting of Mg, Ca, Sr, Ba ions and mixtures thereof.

5. A process according to claim 1 wherein said molecular sieve comprises SAPO-11 and said cation is selected from the group consisting of divalent Mg ions, Ca ions, and mixtures thereof.

6. A process according to claim 1 wherein said n-olefin is selected from the group consisting of n-butene, n-pentene, n-hexene, and mixtures thereof.

7. A process according to claim 1 wherein said n-olefin is n-butene, said conversion is skeletal isomerization reaction, and said different unsaturated compounds comprise isobutene.

8. A process according to claim 1 wherein said dimerization is carried out at a temperature in the range of from about 80° C. to about 250° C. and a pressure greater than about 10 MPa.

9. A process according to claim 1 wherein said catalyst comprises SAPO-11 and said cations are selected from the group consisting of nickel, magnesium, and mixtures thereof.

10. A process comprising
incorporating cations at a surface of a molecular sieve catalyst to produce Lewis acid sites at said surface, wherein said cations are selected from the group consisting of magnesium, calcium, strontium, barium, copper, nickel, cobalt, and mixtures thereof,
contacting said catalyst with n-butene under given conditions,
wherein said conditions are effective to achieve dimerization of said n-butene to produce a reaction product comprising octene, wherein said molecular sieve catalyst is used in the absence of activation with steam prior to contacting said catalyst with said n-olefin.

11. A process according to claim 10 wherein said isomerization is carried out at a temperature in the range of from about 250° C. to about 500° C. and a pressure in the range of from about 0.08 MPa to about 0.12 MPa.

12. A process according to claim 10 further comprising subjecting said reaction product to cracking conditions to produce a cracking product selected from the group consisting of propene, pentenes, and mixtures thereof.

13. A process comprising
incorporating cations at a surface of a molecular sieve catalyst to produce Lewis acid sites at said surface, wherein said cations are selected from the group consisting of magnesium, calcium, strontium, barium, copper, nickel, cobalt, and mixtures thereof,
contacting said catalyst with n-butene under given conditions,
wherein said conditions are effective to achieve skeletal isomerization of said n-butene to produce a reaction product comprising isobutene, wherein said molecular sieve catalyst is used in the absence of activation with steam prior to contacting said catalyst with said n-olefin.

* * * * *